United States Patent [19]

Fishlock-Lomax

[11] Patent Number: 4,946,136
[45] Date of Patent: Aug. 7, 1990

[54] SHAMPOO COMPOSITIONS AND OTHER MILD WASHING PRODUCTS CONTAINING TWO AMPHOTERIC AND ANIONIC SURFACTANTS

[75] Inventor: Eric G. Fishlock-Lomax, Chipping Warden, England

[73] Assignee: Amphoterics International Limited, Leamington Spa, United Kingdom

[21] Appl. No.: 187,926

[22] Filed: Apr. 29, 1988

Related U.S. Application Data

[63] Continuation-in-part of Ser. No. 10,964, Feb. 4, 1987, abandoned, Continuation of Ser. No. 727,081, Apr. 25, 1985, abandoned.

[30] Foreign Application Priority Data

Apr. 25, 1984 [GB] United Kingdom ............... 8410403

[51] Int. Cl.$^5$ .................. A61K 7/075; A61K 7/50; C11D 1/88; C11D 1/94
[52] U.S. Cl. .................................... 252/546; 252/550; 252/551; 252/DIG. 5; 252/DIG. 7; 252/DIG. 14; 424/70
[58] Field of Search ............. 252/527, 546, DIG. 5, 252/DIG. 13, DIG. 7; 424/70

[56] References Cited

U.S. PATENT DOCUMENTS

| | | | |
|---|---|---|---|
| 2,833,722 | 5/1958 | Funderburk | 252/546 |
| 2,929,788 | 3/1960 | Freese | 252/527 |
| 3,072,690 | 1/1963 | Lee | 252/546 |
| 3,280,074 | 10/1966 | McCaleb et al. | 260/47 |
| 3,341,460 | 9/1967 | Wei | 252/546 |
| 3,400,198 | 9/1968 | Lang | 424/71 |
| 3,697,452 | 10/1972 | Olson | 252/545 |
| 4,414,128 | 11/1983 | Goffinet | 252/111 |
| 4,490,355 | 12/1984 | Desai | 424/70 |

FOREIGN PATENT DOCUMENTS 0160507 11/1985 European Pat. Off. ........... 252/546
710705 6/1954 United Kingdom .

OTHER PUBLICATIONS

"Amphoterics Handbook", Green Section, pp. II-a-1-III-s-4.
"Ampholak QTE", Amphoterics International Limited, Oxon, England, Jun. 1984.
Polyram, "N-Alkyl Polypropylene Polyamines", pp. 95–98.
"Cationic Derivatives", Pierrefitte-Auby, Paris, France, pp. 19-21 and 27.
"Fatty Amines and Derivatives–Properties and Uses", Hoechst Aktiengesellschaft, Frankfurt, West Germany, p. 18.

Primary Examiner—Dennis Albrecht
Attorney, Agent, or Firm—Bacon & Thomas

[57] ABSTRACT

Shampoo and similar compositions containing at least two different amphoteric surfactants together with an anionic surfactant are described, at least one of the amphoteric surfactants being of the alkylamino or alkoxyalkylamino type and the other being of the acylamino type.

3 Claims, No Drawings

SHAMPOO COMPOSITIONS AND OTHER MILD WASHING PRODUCTS CONTAINING TWO AMPHOTERIC AND ANIONIC SURFACTANTS

This application is a continuation-in-part of application Ser. No. 010964, filed 02/04/87, now abandoned, which is a continuation of Ser. No. 06/727,081, filed 04/25/85, now abandoned.

This invention relates to shampoo compositions which are intended for frequent use and which contain a hair conditioner which does not build up on the hair, and also to other similarly formulated mild washing products.

Conditioning agents currently used are usually cationic surfactants such as stearyl dimethyl benzyl ammonium chloride, cetrimide, or other quaternary ammonium compounds, or cationic polymers i.e. polymers containing a multiplicity of cationic groups such as quaternary ammonium groups. Betaines may also be used for this purpose. These types of conditioning agents are strongly substantive to the hair and, whilst they are ideal for occasional use, they have the disadvantage when used frequently of building up on the hair with the undesirable effect of making the hair go greasy more easily and more quickly. This is the opposite of the desired effect and can give he hair a lank appearance. This effect is often referred to as "over-conditioning" Said conditioning agents, including quaternary ammonium compounds and betaines, are often highly irritating to the eyes whether used separately or in combination with other ingredients including normal shampoo ingredients. Cationic conditioning agents and anionic shampoo ingredients can also interact and mutaly detract from their performance as conditioners and washing agents respectively.

One of the objects of this invention is to provide a combined shampoo and conditioning product which is very mild to eyes and skin. Another object of this invention is to provide such a product which does not build up on the hair to cause undesirable effects such as "over-conditioning".

The invention thus provides a shampoo composition or other mild washing product containing (a) at least one amphoteric surfactant of the general formula (I) below and (b) at least one amphoteric surfactant of general formula (II) below

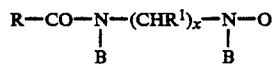 (I)

and

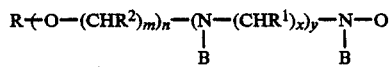 (II)

where R is a $C_{8-20}$ hydrocarbyl group, optionally substituted;
$R^1$ is H or $C_{1-6}$ alkyl;
$R^2$ is H or $C_{1-6}$ alkyl;
B is H, alkyl or substituted alkyl, or a group Q as defined below;
Q is an anionic moiety;
x is 2 to 6;
y is 1 to 5;
m is 2 to 6; and
n is 0 to 10; together with (c) at least one anionic surfactant.

The (first) surfactant of formula (I) generally acts as a low or non-irritant cleaner and the (second) surfactant of formula (II) primarily functions as a conditioner. The formula (II) surfactants also have better detoxification properties and produce less foam, and can be less soluble (particularly when R is tallow-based).

In formulae I and II, R may be for example an alkyl, alkenyl or cycloalkyl group, an aralkyl or aralkenyl group in which the alkyl or alkenyl portion contains at least 6 carbon atoms; or the hydrocarbyl portion of a resinic acid containing at least two fused rings, e.g. as in the tricyclic pine resin acids such as abietic acid. In formula (I) R is preferably a $C_{10-16}$ alkyl group, e.g. a $C_{12}$ group. R may for example be the hydrocarbyl portion of lauric or coconut fatty acid, both of which contain a high proportion of $C_{12}$ constitutents. In formula (II) R is preferably a $C_{12-20}$ alkyl group, e.g. a $C_{18}$ constituent. An example of an unsaturated R group is oleyl. R may for example be substituted by hydroxy, as in hydroxystearyl, R may also be a branched hydrocarbyl group as may be present in synthetic long chain acids.

$R^1$ is usually a hydrogen atom, but may be an alkyl group such as methyl.

Where B is an alkyl group, it may have 1–6, preferably 2–4, carbon atoms, and is preferably a straight chain qroup. Examples of such groups are methyl and ethyl. The alkyl group may be substituted, for example by hydroxy, as in 2-hydroxyethyl, or by amino.

The group Q may for example be of the formula $R^3COOM$ where $R^3$ is a $C_{1-6}$ alkylene group (such as methylene or ethylene) and M is hydrogen or an alkali metal, alkaline earth metal, ammonium or substituted ammonium ion (e.g. mono-, di- or tri-hydroxyethyl ammonium). M is preferably sodium, and $R^3$ is preferably methylene or ethylene.

In Formula (I), x is preferably 2.

The compounds of Formula (I) are for example made by reacting a fatty acid (such as coconut fatty acid) with a substituted diamine such as aminoethylethanolamine to form a 1-hydroxyethyl 2-alkyl imidazoline. The substituent on the diamine, in this case hydroxyethyl, suppresses formation of undesirable by-products such as diamides which would result from use of a symmetrical diamine. N methyl or N-ethyl ethylenediamine may be used similarly in place of aminoethylethanolamine (N-hydroxyethyl ethylenediamine) giving compounds where B is methyl or ethyl instead of hydroxyethyl in one of the positions indicated.

The imidazoline so produced is then reacted further, usually in aqueous conditions, with sodium monochloracetate or with acrylic acid or an ester such as methyl acrylate. These examples provide Q groups of formula $-CH_2COOH$ and $-CH_2CH_2COOH$ respectively which can be utilised in the equivalent form of sodium, potassium, or other salts such as ammonium or triethanolamine salts.

In the preferred example of reacting with sodium monochloracetate and caustic soda, a complex mixture is produced of which the following structures have been quoted as components:

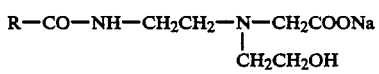

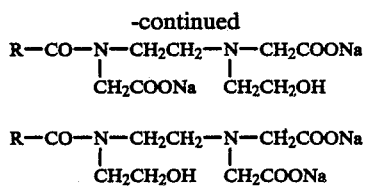

These examples show B as H, hydroxyethyl and carboxymethyl.

Examples of suitable materials of the formula (I) type are these known as cocoamphocarboxyglycinate and cocoamphoglycinate. A specific product of this type is Ampholak XCO-30 (Amphoterics International Limited).

In Formula (II), n is usually 0, B is preferably H or a group Q (in particular where the majority or all of the B groups are 0), x is preferably 3 and y is preferably 2 or 3. The compounds of formula (II) are for example made by first producing a polyamine by successive addition of acrylonitrile and hydrogenation from a fatty primary amine such as tallow amine.

Alternatively the parent alkylamine may have a branched hydrocarbyl chain or may contain an inert group such as an ether group, the latter being examples of compounds in which n is greater than 0.

For example, such a process yields successively:

R—NH—CH₂CH₂CH₂—NH₂

R—NH—CH₂CH₂CH₂—NH—CH₂CH₂CH₂—NH₂

R—NH—CH₂CH₂CH₂—NH—CH₂CH₂CH₂—NH₂CH₂CH₂CH₂—NH₂

As the yield of each stage is not total, a complex mixture of such intermediates will result. There is also a slight chance of small proportions of branched chain structures being produced such as for example:

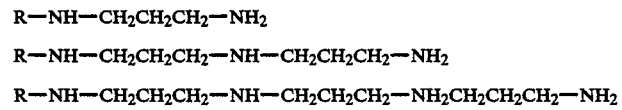

For such intermediates as described above, with 4 N atoms per molecule, y is 3. In practice the average number of N atoms per molecule is about 3.75 making y equal to about 2.75.

Such a polyamine is then further reacted as above with for example sodium monochloracetate or with acrylic acid in a manner well known to those conversant with the art. Whilst sodium monochloracetate and acrylic acid are convenient agents for the introduction of anionic moieties, other agents may similarly be used to produce equivalent results.

One of the objects of this invention is to provide a combined shampoo and conditioning product which is very mild to eyes and skin. A product of Formula (II) was made of the following structure:

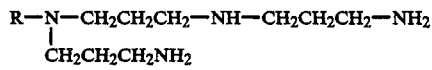

where R was derived from tallow fatty acid and the average value of y was found to be 2.75, so that the product contained an average value of 3.75 N atoms per molecule. This product is hereinafter referred to as 7TX, and is available from Amphoterics International Limited of Sydenham Industrial Estate, Leamington Spa CV31 1PS, England. A similar product from the same manufacturer is Ampholak QTE.

Magnusson and Kligman Tests were conducted by Toxicol Limited on the product 7TX at 30% active matter in water neutralised to a pH of 7.0. Irritation Dose Ranging Results showed complete zero figures after 24 and 48 hours at 100%, 50%, 25% and 12.5% of the supplied sample concentration. The Challenge Phase Results at 100% and 50% of the supplied concentration were again complete zeros after 24 and 48 hours. On challenge with the test material no visible response was exhibited by any animal in the test or control group when challenged with the undiluted test material and a 50% aqueous concentration of the test material.

The following Eye Irritation Studies were all carried out by the same Laboratory according to a method designed to meet the requirements of the test for eye irritants described in the U.S. Federal Hazardous Substances Act. (U.S. Federal Register, 1973, Vol. 38, No. 187, Section 1500: 42 and revised annually in the U.S. Code of Federal Regulations, Subchapter C—Federal Hazardous Substances Act Regulations, Title 16, Part 1500: 42).

The test material 7TX was first compared at full strength as above with other well known types of amphoteric surfactant, all being at 30% active matter and neutralised to pH 7.0. The results are as shown in Table 1 below:

TABLE 1

| Product | Total | Animals Responding | Classification |
| --- | --- | --- | --- |
| Cocoamidopropyl betaine | 88.5 | 6 | Positive |
| Cocoamphocarboxyglycinate | 26.5 | 5 | Positive |
| Test Product 7TX | 7.2 | 1 | Negative |

Cocoamphocarboxyglycinate and Test Product 7TX were next tested for their ability to reduce the irritation of anionic surfactants when mixed together in shampoo type formulations as detailed below:

TABLE 2

| Component | A | B | C |
| --- | --- | --- | --- |
| Test Product 7TX | 5.7 | 9.7 | 0.0 |
| Cocoamphocarboxyglycinate | 4.0 | 0.0 | 9.7 |
| Texapon N25 (1) | 11.8 | 11.8 | 11.8 |
| Texapon K12 (2) | 1.4 | 1.4 | 1.4 |
| Water to 100 parts, neutralised to pH 7.0 with citric acid. | | | |
| Amphoteric net active | 2.91% | 2.91% | 2.91% |
| Anionic net active | 4.38% | 4.38% | 4.38% |
| Anionic/Amphoteric Ratio | 3:2 | 3:2 | 3:2 |

The anionic surfactants used in the Example were
(1) sodium lauryl ether sulfate (27% active) and
(2) sodium lauryl sulfate (84% active).

It will be seen that all variables are held constant except for the relative proportions of the two amphoterics used. This variable is compared in Table 3 below with the Eye Irriatation Draize scores:

TABLE 3

| | Ratio of |

TABLE 3-continued

| | Amphoteric Components | | |
|---|---|---|---|
| Test Product 7TX | 0.0 | 5.7 | 9.7 |
| Cocoamphocarboxyglycinate | 9.7 | 4.0 | 0.0 |
| | Eye Irritation scores | | |
| Cornea | 5.8 | 0.8 | 0.0 |
| Iris | 5.8 | 5.0 | 1.7 |
| Conjunctivae | 15.3 | 7.7 | 5.0 |
| Total | 26.9 | 13.5 | 6.7 |

Thus the admixture of 7TX with cocoamphocarboxyglycinate has approximately halved the Draize score and especially the corneal irritation has been dramatically reduced.

For purposes of comparison, the following Eye Irritation Results were found under identical conditions on various commercial shampoos:

TABLE 4

| Product | Cornea | Iris | Conj |
|---|---|---|---|
| Frequent Use Shampoo (A) | 19.2 | 6.7 | 17.7 |
| Frequent Use Shampoo (B) | 8.3 | 9.2 | 21.0 |
| Baby Shampoo (C) | 3.3 | 5.0 | 12.7 |

From the above it is evident that the formulations of this invention are substantially less irritant than commercial frequent use shampoos on the market and more akin to baby shampoos in their irritation properties.

A further object of this invention is to provide shampoo products with conditioning properties which do not over-condition or build up on the hair.

The following formulation was tested by a consumer panel to compare its properties with the separate shampoo and conditioner, that is under circumstances where neither shampoo nor conditioning agent were mixed together in the same formulation and could not therefore mutually detract from their separate functions of cleaning and conditioning the hair:

| Cocoamphocarboxyglycinate | 20% |
|---|---|
| Test Product 7TX | 5% |
| Sodium lauryl ether sulfate | 25% |
| water to 100% | |

The formulation was neutralised to pH 6.5 with citric acid solution.

More than 75% of the panel were of the opinion that the test formulation functioned as well as or better than separate shampoo and conditioner and the softness of the hair was particularly remarked upon in comparison with separate use of shampoo and normal commercial hair conditioning products. Such softness of the hair is the opposite effect to overconditioning and was maintained through frequent use.

The mildness of said amphoterics and their ability to further reduce the irritation of anionic surfactants with which they are mixed is also useful for other washing products including facial cleansers, liquid soaps and hand cleaners, foam baths and shower gels and mild detergent products for hand washing or clothes or dishes.

Surprisingly other properties were found to be improved also. The partial replacement of cocoamphocarboxyglycinate by 7TX was found to increase lathering properties and to thicken the product so obviating or decreasing the need for additional agents.

As indicated above, the compositions of the invention contain an anionic surfactant, which may be of any kind suitable for use in shampoos. Examples of suitable materials are sodium $C_{9-15}$ alkyl sulfates or ether sulfates (containing for example 1-4 moles ethylene oxide/mole) and the corresponding ammonium, mono-, di- and tri-ethanolamine salts. The anionic surfactant is preferably sodium lauryl sulfate or a sodium lauryl ether sulfate containing 1-4 (preferably 2 or 3) moles of ethylene oxide. (Anionic surfactants of this type are normally supplied on a 27-30% active basis).

For improved cleaning coupled with mildness the ratio of amphoteric to anionic can for example be 2:1 or 3:2 down to 1:1 by weight whilst still retaining mildness to eyes and skin comparing directly with good baby shampoos. Due to the improved reduction in irritation exhibited by the 7TX type of structure it can be used in smaller proportions in relation to the anionic component of down to 1:5 amphoteric to anionic ratio. In this case the coco amphocarboxyglycinate is best reduced in favour of the 7TX type of structure.

Examples of suitable compositions are:

First type of amphoteric (1):5-50% (preferably 5-25%)

Second type of amphoteric (2):1-50% (preferably 1-5%)

Anionic surfactant:5-50% (preferably 5-25%).

(1) this may be of Formula (I) above where R is preferably derived from coco fatty acid.

(2) this is of Formula (II) above, where R is preferably derived from tallow fatty acid.

The compositions of the invention are water-based and if desired may contain additional ingredients such as normally included in shampoos, for example preservatives, foam boosters (such as lauric diethanolamide or amine oxide), oils (such as jojoba or lemon), dyes and fragrances.

I claim:

1. A shampoo composition or other mild washing product which contains (a) at least one amphoteric surfactant of formula (I) and (b) at least one amphoteric surfactant of formula (II) together with (c) at least one anionic surfactant; said composition containing 5-50% of one or more surfactants of formula (I), 1-50% of one or more surfactants of formula (II) and 1-50% of one or more anionic surfactants (by weight of the total composition); said formula (I) being:

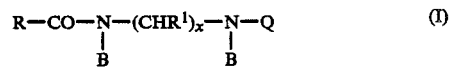

in which for formula (I) R is a $C_{8-20}$ hydrocarbyl group, optionally substituted by hydroxy; $R^1$ is H or $C_{1-6}$ alkyl; B is H, $C_{1-6}$ alkyl, optionally substituted by hydroxy or amino, or a group Q; Q is a group $-R^3COOM$ where $R^3$ is a $C_{1-6}$ alkylene group and M is $-H$ or an alkali metal, alkaline earth metal, ammonium or hydroxy ethyl-substituted ammonium ion; and x is 2 to 6; formula (II) being:

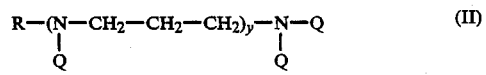

in which for formula (II) R is a $C_{12-20}$ alkyl group; Q is $-CH_2COOM$ or $-CH_2CH_2COOM$; M is $-H$ or an alkali metal, alkaline earth metal, ammonium or hydroxy ethyl-substituted ammonium ion; and y is 2 or 3.

2. A composition according to claim 1, in which in the surfactant of formula (I), R is a $C_{10-16}$ alkyl qroup, $R^1$ is H, Q is —$CH_2COOM$ and x is 2.

3. A composition according to claim 1 containing at least one surfactant of formula (I) in which R is the hydrocarbyl portion of lauryl or coconut fatty acid, $R^1$ is H, B is H, —$CH_2CH_2OH$ or a group Q, Q is —$CH_2COOM$ and x is 2.

* * * * *